United States Patent [19]

Christenson

[11] Patent Number: 5,571,939
[45] Date of Patent: Nov. 5, 1996

[54] METHOD FOR PREPARING DODECAHYDRO-3A,6,6,9A-TRETRAMETHYLNAPHTHO[2,1-B]FURAN AND NOVEL HALOETHYL DECALIN DERIVATIVES

[75] Inventor: Philip A. Christenson, Midland Park, N.J.

[73] Assignee: BASF Corporation, Mount Olive, N.J.

[21] Appl. No.: 503,118

[22] Filed: Jul. 17, 1995

Related U.S. Application Data

[62] Division of Ser. No. 104,317, Aug. 9, 1993, Pat. No. 5,434,300, which is a division of Ser. No. 408,876, Sep. 18, 1989, Pat. No. 5,235,098, which is a continuation-in-part of Ser. No. 65,426, Jun. 23, 1987, abandoned.

[51] Int. Cl.$^6$ ...................... C07C 69/013; C07D 311/92; C07D 303/14
[52] U.S. Cl. ..................... 560/256; 549/389; 549/560
[58] Field of Search ........................ 560/256; 549/560, 549/389

[56] References Cited

U.S. PATENT DOCUMENTS

| | | | |
|---|---|---|---|
| 2,181,085 | 11/1939 | Alquist et al. | 260/348 |
| 3,029,255 | 4/1962 | Stoll | 260/345.2 |
| 3,050,532 | 8/1962 | Schumacher et al. | 260/343.3 |
| 3,671,587 | 6/1972 | Troxler et al. | 260/570.7 |
| 3,989,739 | 11/1976 | Stadler et al. | 260/486 R |
| 5,235,098 | 8/1993 | Christenson | 560/256 |
| 5,434,300 | 7/1995 | Christenson | 560/256 |

OTHER PUBLICATIONS

Cambie et al., *Aust. J. Chem.*, 24, pp. 583–591 (1971).

*Primary Examiner*—Gary Geist
*Assistant Examiner*—Barbara S. Frazier
*Attorney, Agent, or Firm*—Kenyon & Kenyon

[57] ABSTRACT

The method is directed to the preparation of dodecohydro-3a,6,6,9a-tetramethyl-naphtho[2,1-b]furan from sclareol using an alkoxy-radical fragmentation reaction. A novel 9-haloethyl decalin derivative is an intermediate in this method.

3 Claims, No Drawings

METHOD FOR PREPARING DODECAHYDRO-3A,6,6,9A-TRETRAMETHYLNAPHTHO[2,1-B]FURAN AND NOVEL HALOETHYL DECALIN DERIVATIVES

CROSS REFERENCE TO RELATED APPLICATIONS

This application is a division of application Ser. No. 08/104,317 filed on Aug. 9, 1993, now U.S. Pat. No. 5,434,300, which is a division of application Ser. No. 07/408,876, filed on Sep. 18, 1989, now U.S. Pat. No. 5,235,098, which is a continuation-in-part of application Ser. No. 07/065,426, filed on Jun. 23, 1987, now abandoned.

BACKGROUND OF THE INVENTION

The compound dodecahydro-3a,6,6,9a-tetramethyl-naphtho[2,1-b]furan (hereinafter Naphthofuran II) is a synthetic congener of Ambergris, a rare perfumery composition of natural origin having a sweet, woody, amber bouquet. Naphthofuran II has been used in perfume compositions and in cleaning formulations, and as a fragrance for toiletries and household products where a persistent amber effect is desired. Naphthofuran II is also a component of tincture of Ambergris and synthetic Naphthofuran II has been used in artificial Ambergris formulations.

Naphthofuran II may be produced synthetically from 3-ethenyldecahydro-2-hydroxy-2,5,5,8a-pentamethyl-1-naphthalenepropanol, commonly known as sclareol. One method for this conversion is a two stage oxidation followed by a hydride reduction and cyclization. See, for example, U.S. Pat. No. 3,050,532; U.S. Pat. No. 3,029,255; and *Aust. J. Chem.*, 1971, 24, 591. Another method involves oxidation of sclareol to sclareol oxide followed by a multi-step synthesis to produce Napthofuran II as a mixture of stereoisomers, as described in *Helv. Chim. Acta*, 1942, 25 621; *J. Chem. Soc.*, 1960, 4613; *Helv. Chim. Acta*, 1950, 33 1251; U.S. Pat. No. 3,029,255, 1962; *Helv. Chim. Acta*, 1950, 33 1308; *J. Am. Chem. Soc.*, 1963, 85 3979); and *Helv. Chim. Acta*, 1951, 34 1664.

These methods, however, lack simplicity and are based upon multiple synthetic reactions. Moreover, they produce undesirable side reactions and do not generate high yields of Naphthofuran II. Accordingly, it is an object of the invention to develop a simple method for the production of Naphthofuran II for sclareol. Another object is the production of a high yield of Naphthofuran II without the complications caused by side reactions.

SUMMARY OF THE INVENTION

These and other objects are achieved by the invention which is directed to a method for the production of Naphthofuran (II) from sclareol. In this method, an alkoxy-radical fragmentation reaction is used to convert sclareol derivatives to a 9-haloethyl decalin derivative of the formula I:

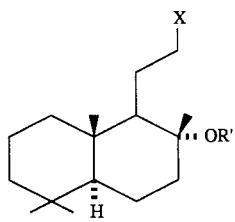

wherein X is iodo, bromo or chloro and R is $C_2$ to $C_5$ alkanoyl. Basic hydrolysis of this 9-haloethyl decalin derivative produces a naphthofuran of the formula II

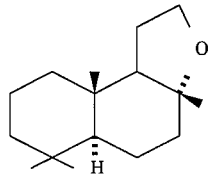

Several alternatives for the alkoxy-radical fragmentation reaction can be used according to the method of the invention. In the first, a sclareol alkanoate derivative of the formula III:

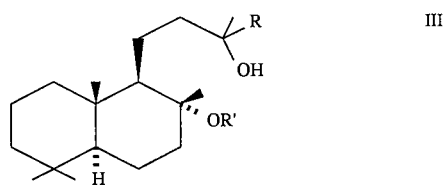

IIIa: R is —CH=$CH_2$, R is $C_2$ to $C_5$ alkanoyl
IIIb: R is CH——CH, R is $C_2$ to $C_5$ alkanoyl
IIIc: R is $CH_2CH_3$, R is $C_2$ to $C_5$ alkanoyl wherein R is vinyl, epoxyethyl or ethyl, and R is as defined above is treated with iodine and an oxidizing agent to produce the decalin derivative of formula I wherein X is iodo.

In the second method, sclareol oxide of the formula IV:

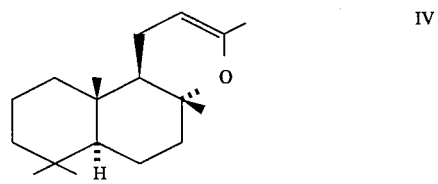

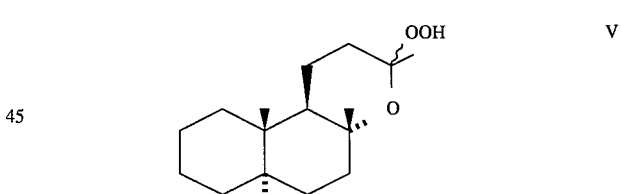

is treated with hydrogen peroxide in the presence of an acid catalyst to produce a peroxide intermediate V which is then treated with a metallic halide reducing agent to produce the decalin derivative of formula I wherein R' is acetyl.

The invention described herein includes the novel 9-haloethyl decalin derivatives of formula I, an epoxysclareol acetate (IIIa) and a sclareol oxide-13-hydroperoxide intermediate V.

DETAILED DESCRIPTION OF THE INVENTION

A process of the present invention produces a high yield of Napthofuran II from sclareol derivatives through steps which employ an alkoxy-radical fragmentation reaction and a hydrolysis. It avoids production of side products that could alter the fragrance qualities of Napthofuran II.

According to one process of the invention, the sclareol alkanoate derivative of formula III can be converted to the decalin derivative of formula I wherein X is iodide by treatment with iodine and an oxidant in an inert solvent. The oxidant can be, e.g., mercuric oxide, lead tetraacetate, iodosobenzene diacetate, periodinane, iodosobenzene or iodoxybenzene. Preferred oxidants include iodosobenzene, lead tetraacetate and iodosobenzene diacetate, the later two being especially preferred. The amount of oxidant used may be from about 50 to about 250 mole percent, about 50 to about 200 mole percent being preferred and about 100 to about 200 mole percent being especially preferred, the mole percentage being measured relative to the molar amount of the sclareol alkanoate derivative present. The reaction may be performed in an inert solvent, such as an aromatic hydrocarbon, an aliphatic hydrocarbon or a halocarbon. Preferred solvents are benzene, toluene, chlorobenzene, xylene, hexane, cyclohexane, dichloroethylene, tetrachloroethane, and carbon tetrachloride. The especially preferred solvents include benzene, carbon tetrachloride and chlorobenzene, with benzene being particularly preferred. The reaction is usually performed in the presence of an acid scavenger such as an amine or an alkali or alkaline earth metal carbonate. Calcium carbonate, pyridine, sodium carbonate and triethylamine are preferred acid scavengers. The reaction may be conducted at a temperature of about 60° C. to about 130° C. with about 70° C. to about 120° C. being preferred and about 75° C. to about 85° C. being most preferred.

The sclareol alkanoate derivatives where R is $C_3$ to $C_5$ alkanoyl can be prepared using the methods of Buchi and Bieman, as described in Example 1, the teachings of which are incorporated herein by reference.

According to another alternative for the alkoxy-radical reaction employed in the process of the present invention, treatment of sclareol oxide with a source for hydrogen peroxide such as hydrogen peroxide itself, or a hydrogen peroxide generating system in an inert solvent in the presence of an alkanoic acid such as acetic acid gives a hydroperoxide intermediate. An example of a hydrogen peroxide generating system which may be useful comprises a mixture of barium peroxide and a protic acid such as acetic acid or carbonic acid. Other protonic or Bronsted acids can also be used. Preferred acids include lower alkyl carboxylic acids, chloro, dichloro and trifluoroacetic acid, formic acid, phosphoric acid and buffers derived from phosphoric acid. Acetic acid is especially preferred. The amount of acid used may be from about 10 to about 5000 mole percent with about 100 to about 4000 mole percent being preferred and about 3500 mole percent being particularly preferred, the mole percentage being measured relative to the amount of sclareol oxide present. Solvents such as dimethoxyethane, dioxane, ethyl ether, t-butanol, ethyl acetate, dichloromethane, tetrahydrofuran, dichoroethane, water t-butyl methyl ether, toluene and hexane may also be used. Preferred solvents are t-butyl methyl ether, t-butanol and tetrahydrofuran, the latter being especially preferred. A useful temperature range is between about 0° C. and about 50° C. with about 10° C. to about 40° C. being preferred and about 20° C. to about 30° C. being the most preferred. The peroxide treatment can take from about 0.5 to about 10 hours, about 0.5 to about 6 hours being preferred and about 3 to 4 hours being especially preferred.

The hydroperoxide intermediate can be fragmented to provide the decalin derivative of formula I wherein X is Cl, Br or I and R' is acetyl upon treatment with an appropriate metal halide reducing agent, such as a ferrous halide and a catalytic amount of a cupric halide, the cupric halide being Cl, Br or I. Other metal halide reducing agents may also be used in this reaction, including halide salts of copper (I), chromium (II), titanium (III), vanadium (II); and alkanols such as methanol, ethanol, isopropanol and t-butanol, as well as water, tetrahydrofuran, dioxane, ether and mixtures thereof may be included. The alcohols, tetrahydrofuran and water are preferred, with methanol being especially preferred. The reaction may be performed in the temperature range of about 0° C. to about 50° C. preferably about 10° C. to about 35° C., most preferably about 30° C. The time for the reaction is fifteen minutes to about 2 hours with about a half hour to about 2 hours being preferred and about a half to 1 hour being especially preferred.

The haloethyl decalin derivatives of formula I where R' is acetyl produced in the foregoing fashion are converted to naphthofuran II in high yield according to the process of the present invention by hydrolysis with a metal hydroxide in an appropriate solvent. Alkali or alkaline earth metal hydroxides are preferred. Potassium hydroxide is the most preferred. A variety of protic or aprotic solvents mixed with water may be used, such as lower alkyl alcohols, ethyl ether, tetrahydrofuran, dioxane, dimethoxyethane, dimethylsulfoxide, ethylene glycol, dimethylformamide, N-methylpyrrolidone or acetonitrile. The preferred solvent is a mixture of water and alcohols or diols, such as, methanol, ethanol, propanol, isopropanol, n-butanol, t-butanol, ethylene glycol. The most preferred solvent is a mixture of water and isopropanol. The reaction may be carried out in the temperature range of about 25° C. to about 150° C. The preferred temperature range is about 50° C. to about 100° C. The most preferred temperature range is about 70° C. to about 85° C.

The process of the present invention may be applied to other labdane derivatives such as manool (VI), larixol (VII), torulosol (VIII) and-cupressic acid (IX) to provide compounds of general formula XI, wherein $R^a$ and $R^b$ are as described in VI–IX with IX equal to halogen.

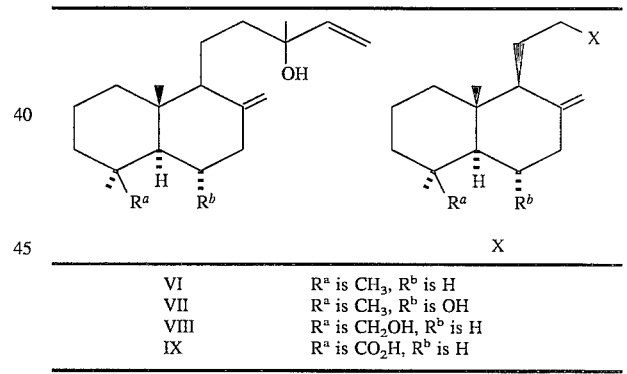

| | |
|---|---|
| VI | $R^a$ is $CH_3$, $R^b$ is H |
| VII | $R^a$ is $CH_3$, $R^b$ is OH |
| VIII | $R^a$ is $CH_2OH$, $R^b$ is H |
| IX | $R^a$ is $CO_2H$, $R^b$ is H |

Compound X may be converted into useful terpenoid derivatives of formula I by reducing the methylene group and treating with alkanoic acid as previously described.

The alkoxy-radical fragmentation can be applied pursuant to reaction procedures such as in Waegell et al., J. Chem Res. S., 1981, 236. The following examples illustrate some further embodiments of the invention.

In certain reactions described herein, conventional protection and deprotection reactions may be used to further enhance yields of preferred copunds. For example, when $R^b$ is hydroxyl, a protective group, e.g., methoxy, may be used, which is then removed using standard deprotection conditions.

Experimental Section

General. Benzene was dried over 4A molecular sieves prior to use. Sclareol, purchased from R.J. Reynolds Tobacco Co, was recrystallized from hexane prior to use. All other reagents and solvents were of reagent grade and were used as received.

IR spectra were obtained with a Perkin-Elmer 710B spectrophotometer. Routine $^1$H-NMR spectral data reported at 250 MHz were recorded on a Bruker WM250 NMR instrument and the $^{13}$C-NMR spectra were obtained on the same instrument at 62.5 MHz. Mass spectra were obtained with a Hewlett-Packard 5985 mass spectrophotometer. Column chromatography way performed with Merck 60 brand of silica gel. GLC analyses were obtained with a Hewlett-Packard Model 5840 or a Perkin-Elmer model 920 gas chromatograph, using either a 6 ft., 2-mm i.d. glass column packed with 3% nonpolar silicone on diatomaceous earth, 100–120 mesh or a 10 ft., 2 mm i.d. glass column packed with 2% polyethylene glycol on diatomaceous earth, 100–120 mesh. Where indicated, percentages refer to computer calculated peak areas without correction for response. Melting points were determined with a Thomas Model 40 micro hot-stage apparatus and are uncorrected. Optical rotations were obtained in chloroform solution at ambient temperature unless otherwise noted using a Perkin-Elmer 241 polarimeter.

EXAMPLE 1

Sclareol Epoxide Derivative

T-butyl hydroperoxide (3mL, 0.027 mol) in $CH_2Cl_2$ (30 mL) was added to a mixture of sclareol monoacetate which may be prepared as described by G. Buchi and K. Bieman in *Croat. Chem. Acta* 1957, 29 163–171 (7.00g, 0.02 mol) vanadium (IV) bis(2,4-pentanedionate) oxide (0.100g, 0.38 mmol) and methylene chloride (60 mL) over a 1h period. The mixture was heated at reflux for 2h and then t-butyl hydroperoxide (1 mL, 0.009 mol) in methylene chloride (15 mL) was added over a 0.5h period. The mixture was heated at reflux for an additional 2h and then stirred at 25° C. The phases were separated and the aqueous phase was extracted with methylene chloride (2×25 mL). The combined organic layers were washed with 10% sodium sulfite solution (2×30 mL) (negative starch iodide test), saturated sodium bicarbonate solution and dried ($Na_2SO_4$). Evaporation of solvents provided 7.038 g of a nearly colorless solid. Crystallization from hexane/ethyl acetate gave 6.399g of [1R-( 1α-(R*),2β, 4aβ,8aα)]-2-acetyloxy-α-oxiranyldecahydro-α ,2,5,5,8a-pentamethyl-1-naphthalenepropanol (IIIb), mp 129.5° C.–131° C.; [α] D-35.75° C. (c, 3.43). $^1$H-NMR (250 MHz, $CDCl_3$) α 0.74 (3H, s), 0.79 (3H, s), 0.82 (3H, s), 1.25 (3H, s), 1.41 (3H, 3), 1.88 (3H, s). 0.9–1.8 (16H, m), 2.51–2.93 (4H, m); $^{13}$C-NMR α 15.68 (q), 18.34 (t), 19.07 (t), 20.01 (t), 20.64 (q), 21.40 (q), 22.79 (q), 25.84 (q), 33.07 (s), 33.28 (q), 38.82 (t), 39.55 (s), 39.66 (t), 41.90 (t), 41.95 (t), 44.03 (t), 55.70 (d), 57.72 (d), 69.41 (s), 88.08 (s), 169.85 (s); IR ($CHCl_3$) v max 3530, 2940, 1720, 1460, 1385, 1360, 1260 $cm^{-1}$; MS, m/e 306, 291, 273, 109, 95, 81, 43. Anal Calcd for $C_{22}H_{38}O_4$: C, 72.09, H, 10.45. Found: C, 72.17; H, 10.45.

EXAMPLE 2

Dihydro Sclareol Derivative

A mixture of sclareol monoacetate (3.50g, 0.01 mol), platinum oxide (0.225g) sodium nitrite (0.01g) and ethanol (40 mL) was shaken under a hydrogen atmosphere (40 psi) for 2.5h. The mixture was filtered through celite and the solids were washed with ethanol. The solvent was evaporated and the residue crystallized from hexane to give 2.69g of [1R-[1α,(S*),2β,4aβ,8aα]]-2-acetyloxy-α-ethyldecahydro-α, 2,5,5,8a-pentamethyl-1-naphthalenepropanol (IIIc), mp 92°–94° C., [α]D-27.35° (C.1.547). See, e.g., D. B. Bigley, N. A. J. Rogers, J. A. Barltrop in *J. Chem. Soc.*, 1960, 4613–4627 and R. K. Grant, C. Huntrakal, and R. T. Weavers, *Aust. J. Chem.* 1972, 25 365–74.) $^1$H-NMR (250 MHz, $CDCl_3$) α 0.78 (3H,s), 0.84 (3H,s), 0.87 (3H,s) 0.90 (3H,t, J=7.5 Hz), 1.16 (3H, s), 1.47 (3H, s), 1.93 (3H, s), 0.8–1.9 (18H, m), 2.60–2.68 (1H, m). IR ($CDCl_3$) v max 3580, 3450, 2950, 1720, 1455, 1485, 1460, 1260 $cm^{-1}$. MS, m/e 352, 292, 274, 259, 245, 204, 137, 109, 95, 43.

EXAMPLE 3

Sclareol Acetate Derivative

A mixture of sclareol monoacetate (1.050g, 0.003 mol), iodosobenzene diacetate (0.966g, 0.003 mol), calcium carbonate (1.2g, 0.012 mol) and benzene (60 mL) was heated at reflux and a solution of iodine (0.762g, 0.003 mol) in benzene 25 mL) was added dropwise over a 45 min period. The mixture was heated at reflux for 1.5h, cooled, decanted from solids, washed with 5% sodium thiosulfate solution (2×30 mL) and dried ($NaSO_4$). The solvent was evaporated and the residue Kugelrohr distilled (bath 60° C., 0.5 mm) to remove most of the iodobenzene. Chromatography (eluant: hexane:ethyl acetate; 20:1) of the residue gave 0.429g of [1R-(1α,2β,4aβ,8aα)]-decahydro- 1-(2-iodoethyl)-2,5,5,8a-tetramethyl-2-naphthalenol acetate, the decalin derivative of formula I wherein X is I and R' is $C(O)CH_3$. Crystallization from hexane provides a pure sample; mp 94°–99° C. with decomposition; [α]D-4.28 (c, 1.33). $^1$H-NMR (250 MHz, $CDCl_3$) α 0.77 (3H, s), 0.81 (3H, s), 0.85 (3H, s), 1.46 (3H, s), 1.93 (3H,s), 0.85–2.1 (13H, m), 2.62–2.73 (1H, m), 3.09–3.35 (2H, m); $^{13}$C-NMR α 7.59 (t), 15.78 (q), 18.32 (t), 19.92 (t), 20.48 (q), 21.43 (q), 22.91 (q), 31.84 (t), 33.16 (s), 33.31 (q), 38.95 (t), 39.26 (t), 39.73 (t), 41.83 (t), 55.66 (d), 61.17 (d), 87.26 (s), 169.73 (s); IR ($CHCl_3$) v max 2940, 1720, 1450, 1385, 1360, 1250 $cm^-$; MS, m/e 346, 331, 279, 219, 137, 109, 95, 43. Anal. Calcd for $C_{18}H_{31}IO_2$: C, 53.20; H, 7.69; I, 31.23. Found: C, 53.76; H, 7.99; I, 30.91.

The reaction also provides 0.639g of [1R-[1R-(1α, 2β, 4aβ, 8aα)]]-1-(5-iodo-3,4-epoxy-3-methylpentyl) decahydro-2,5,5,8a-tetramethyl-2-naphthalenol acetate as a mixture of isomers. $^1$H-NMR (250 MHz, $CDCl_3$) 0.78 (3H, s), 0.81 (3H, s), 0.86 (3H, s), 1.28 and 1.34 (3H, 2s), 1.46 and 1.47 (3H, 2s), 1.930 and 1.932 (3H, 2s), 0.8–2.0 (15H, m), 2.6–2.75 (1H, m), 2.9–3.4 (3H, m); IR ($CDCl_3$) v max 2930, 1720, 1455, 1385, 1360, 1255 $cm^{-1}$. MS, m/e 416, 401, 384, 289, 245, 204, 137, 109, 95, 43.

EXAMPLE 4

Sclareol Acetate Derivative

To a mixture of lead tetraacetate [5.32g, 0.012 mol, washed with hexane (2×50 mL)], calcium carbonate (2.40g, 0.024 mol) sclareol monoacetate (2.10g, 0.006 mol) and benzene (150 mL) heated at reflux was added a solution of iodine (1.524g, 0.006 mol) in benzene (90 mL) over a 1.5h period. The mixture was heated at reflux for 1h, cooled and filtered. The filtrate was washed with 5% sodium thiosulfate solution (2×50 mL), saturated sodium bicarbonate solution, dried ($Na_2SO_4$) and evaporated. Chromatography (eluant: hexane:ethyl acetate; 20:1) gave 1.209g of the iodoacetate (I; X=I, R'=$C(O)CH_3$) and 0.906g of iodoepoxide. The compounds were characterized as described in Example 3.

EXAMPLE 5

Decalin Derivative

A mixture of epoxide (IIIb) (0.732G, 0.002 mol, from Example 1) iodosobenzenediacetate (1.288g, 0.004 mol), calcium carbonate (0.8g, 0.008 mol) and benzene (40 mL) was heated at reflux and a solution of iodine (0.508g, 0.002 mol) in benzene (25 mL) was added dropwise over a 45 min period. The mixture was heated at reflux for 1.5h and cooled to provide 0.433g of the decalin derivative of formula I wherein X is I and R' is C(O)CH$_3$. Work-up and chromatography were as described in Example 3.

EXAMPLE 7

Decalin Derivative

A mixture of lead tetraacetate (3.547g, 0.008 mol), calcium carbonate (1.60g, 0.016 mol), the dihydrosclareol derivative of Example 2 (1.418g, 0.004 mol) and benzene (200 mL) was heated at reflux and a solution of iodine (1.016g, 0.004 mol) in benzene (50 mL) was added over a 1.5h period. The mixture was heated at reflux for 1h, cooled and filtered. Work-up and chromatography as described in Example 4 gave 0.794g of the decalin derivative of formula I wherein X is I and R is C(O)CH$_3$ and 0.388g of 13-nor-vinyl-13-ketosclareol acetate which was identical to an authentic sample as reported by D. B. Bigley, N. A. J. Rogers, J. A. Barltrop in *J. Chem. Soc.*, 1960 4613–4627.

EXAMPLE 8

Decalin Derivative

Acetic acid (2 mL) was added to a mixture of sclareol oxide (IV) (0.262g, 0.001 mol, which may be prepared as described by D. B. Bigley, N. A. J. Rogers and J. A. Barltrop in *J Chem. Soc.*, 1960, 4613–4627), tetrahydrofuran (8 mL), and 30% hydrogen peroxide (6 mL). The mixture was stirred at 25° C. for 4h, poured onto water (10 mL) and extracted with hexane/ethyl acetate (9:1, 4×10 mL). The extracts were washed with water (2×5 mL), saturated sodium bicarbonate solution (2×10 mL) and dried (Na$_2$SO$_4$). Evaporation of solvents provided 0.327g of the hydroperioxide intermediate as a colorless solid. $^1$H-NMR (60 MHz, CDCl$_3$) α 0.080 (6H, s), 0.87 (3H, s) 1.38 (3H, s), 1.43 (3H, s), ) 0.8–2.2 (16H, m) 7.52 (1H, s).

A solution of the hydroperoxide intermediate (0.001 mol) in methanol (10 mL) was added dropwise over a 30 min period to a solution of ferrous chloride (0.398g, 0.002 mol) and cupric chloride (0.034g, 0.0002 mol) in methanol (6 mL) at 25° C. The mixture was stirred at 25° C. for 15 min. The mixture was poured onto water (20 mL) and extracted with hexane ethyl acetate (9:1, 4×15 ml). The extracts were washed with water (2×10 mL), saturated sodium bicarbonate solution (2×10 mL) and dried (Na$_2$SO$_4$). The solvents were evaporated and the residue chromatographed to provide 0.229g of [1R-[1α, 2β4aβ, 8aα)] decahydro-1-(2-chloroethyl)-2,5,5,8a-tetramethyl- 2-naphthalenol acetate, the decalin derivative of formula I wherein X is Cl and R' is C(O)CH$_3$. Recrystallization from hexane provided an analytical sample. mp 99°–101.5° C., [α]D-15.76 (c, 1.76). $^1$H NMR (250 MHz, CDCl$_3$) α 0.73 (3H, s), 0.78 (3H, s), 0.81 (3H, s), 1.43 (3H, s), 1.87 (3H, s), 0.7–2.05 (13H, m), 2.6–2.7 (1H, m), 3.36–3.59 (2H, m); $^{13}$C-NMR α 15.56 (q), 18.28 (t), 19.87 (t), 20.39 (q), 21.37 (q), 22.65 (q), 29.88 (t), 33.07 (s), 33.22 (q), 38.87 (t), 39.09 (s), 39.68 (t), 41.78 (t), 45.76 (t), 55.59 (d), 56.93 (d), 87.00 (s), 169.30 (s) ; IR (CHCl$_3$) v max 2930, 1725, 1460, 1440, 1390, 1370, 1255 cm$^{-1}$; MS, m/e 272, 256, 254, 241, 239, 137, 124, 109. Anal. Calcd for C$_{18}$H$_{31}$ClO$_2$: C, 68.65; H, 9.92; Cl, 11.26. Found: C, 68.82; H, 10.08; Cl, 11.12.

EXAMPLE 10

Decalin Derivative

[1R-(1α, 2β, 4aβ, 8aα)]-Decahydro-1-(2-bromoethyl)-2,5,5,8a-tetramethyl-2-naphthalenol acetate The decalin derivative of formula I wherein X is Br may be prepared by reaction of the hydroperoxide intermediate of Example 9 with ferrous bromide and cupric bromide in a manner similar to that described in Example 9.

EXAMPLE 11

Dodecahydro-3a,6,6,9a-tetramethylnaphtho[2,1-b]furan

A mixture of the decalin derivative of formula I wherein X is I and R' is C(O)CH$_3$ (0.610g, 0.0015 mol from any of Examples 3 through 8), potassium hydroxide (0.953g, 0.009 mol), isopropanol:water (6:1, 50 mL) was heated at reflux for 18h. The mixture was cooled and concentrated under reduced pressure. The residue was added to water and extracted with hexane (4×20 mL). The extracts were washed with water (15 mL), brine (15 mL) and dried (Na$_2$SO$_4$). The solvents were evaporated and the residue chromatographed (eluant; hexane:ethyl acetate; 20:1). Kugelrohr distillation (bath 120° C., 1mm) gave 0.286g of compound II, mp 74.5°–76° C.; [α]D- 29.90° (c, 3.01 benzene); literature reference: mp 75°–76° C., [α]D-28.0° (benzene) see M. Stoll and M. Hinder in *Helv. Chim. Acta*, 1953, 36, 1995–2008; NMR(250 MHz, CDCl$_3$) α 0.83 (6H, s), 0.88 (3H, s), 1.08 (3H, s), 0.8–2.0 (14H, m), 3.75–3.96 (2H, m); $^{13}$C-NMR α 15.06 (q), 18.47 (t), 20.72 (t), 22.69 (2q), 33.10 (s), 36.27 (s), 39.36 (t), 40.06 (t), 42.54 (t), 57.36 (d), 60.22 (d), 64.94 (t), 79.84 (s); IR (melt) v max 2930, 1480, 1460, 1390, 1375 cm$^{-1}$; MS, m/e 236, 221, 204, 137 97.

EXAMPLE 12

Dodecahydro-3a,6,6,9a-tetramethylnaphtho[2,1-b]furan

A mixture of the decalin derivative of forumla I wherein X is Cl and R' is C(O)CH$_3$ (0.124g, 0.36 mmol from Example 9) potassium hydroxide (0.118g) isopropanol (10mL) and water (1.5 mL) was reacted as described in Example 11 to provide after work-up and kugelrohr distillation 0.077g of Napthofuran II.

While certain preferred embodiments have been described herein in detail, numerous alternative embodiments are possible and contemplated as falling within the scope of the invention described herein. Consequently, the claims are not to be so limited.

I claim:

1. A decalin derivative of the formula

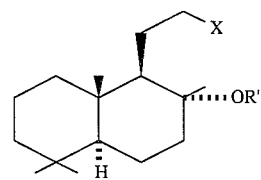

wherein X is chloro, bromo, or iodo and R' is $C_2$ to $C_5$ alkanoyl.
2. An epoxysclareol acetate of the formula:
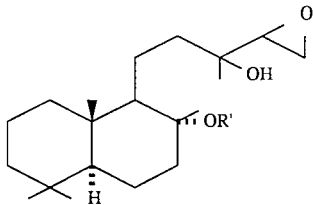
where R' is $C_2$ to $C_5$ alkanoyl.
3. A sclareol oxide-13-hydroperoxide intermediate of the formula:
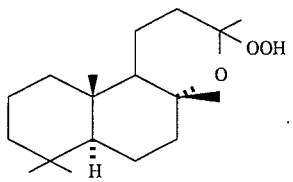
* * * * *